(12) United States Patent
Sun et al.

(10) Patent No.: US 11,488,021 B2
(45) Date of Patent: Nov. 1, 2022

(54) SYSTEMS AND METHODS FOR IMAGE SEGMENTATION

(71) Applicant: SHANGHAI UNITED IMAGING INTELLIGENCE CO., LTD., Shanghai (CN)

(72) Inventors: Shanhui Sun, Lexington, MA (US); Pingjun Chen, Gainesville, FL (US); Xiao Chen, Lexington, MA (US); Zhang Chen, Brookline, MA (US); Terrence Chen, Lexington, MA (US)

(73) Assignee: SHANGHAI UNITED IMAGING INTELLIGENCE CO., LTD., Shanghai (CN)

( * ) Notice: Subject to any disclaimer, the term of this patent is extended or adjusted under 35 U.S.C. 154(b) by 114 days.

(21) Appl. No.: 16/905,115

(22) Filed: Jun. 18, 2020

(65) Prior Publication Data
US 2021/0397966 A1 Dec. 23, 2021

(51) Int. Cl.
| | |
|---|---|
| *G06T 7/10* | (2017.01) |
| *G16H 30/40* | (2018.01) |
| *G06N 3/08* | (2006.01) |
| *G06K 9/62* | (2022.01) |
| *G06N 3/04* | (2006.01) |

(52) U.S. Cl.
CPC .......... *G06N 3/084* (2013.01); *G06K 9/6261* (2013.01); *G06N 3/0454* (2013.01); *G06T 7/10* (2017.01); *G16H 30/40* (2018.01); *G06T 2207/20081* (2013.01); *G06T 2207/20084* (2013.01)

(58) Field of Classification Search
None
See application file for complete search history.

(56) References Cited

U.S. PATENT DOCUMENTS

| | | | |
|---|---|---|---|
| 10,426,442 B1* | 10/2019 | Schnorr | A61D 19/02 |
| 2019/0244362 A1* | 8/2019 | Movshovitz-Attias | G06T 7/136 |
| 2020/0134815 A1* | 4/2020 | Ezhov | G06N 3/0445 |
| 2020/0222018 A1* | 7/2020 | van Walsum | A61B 6/5264 |
| 2020/0302224 A1* | 9/2020 | Jaganathan | G06N 3/084 |
| 2020/0395117 A1* | 12/2020 | Schnorr | G16H 30/40 |

* cited by examiner

*Primary Examiner* — Idowu O Osifade
(74) *Attorney, Agent, or Firm* — Zhong Law, LLC

(57) ABSTRACT

Described herein are neural network-based systems, methods and instrumentalities associated with image segmentation that may be implementing using an encoder neural network and a decoder neural network. The encoder network may be configured to receive a medical image comprising a visual representation of an anatomical structure and generate a latent representation of the medical image indicating a plurality of features of the medical image. The latent representation may be used by the decoder network to generate a mask for segmenting the anatomical structure from the medical image. The decoder network may be pre-trained to learn a shape prior associated with the anatomical structure and once trained, the decoder network may be used to constrain an output of the encoder network during training of the encoder network.

20 Claims, 6 Drawing Sheets

SYSTEMS AND METHODS FOR IMAGE SEGMENTATION

BACKGROUND

Medical imaging plays an important role in modern day healthcare services. With advanced imaging equipment such as ultrasound scanners, X-ray machines, medical resonance imaging (MRI) scanners, computed tomography (CT) scanners, and positron emission tomography (PET) scanners, valuable image data can be generated to identify a plurality of anatomical structures and/or possible abnormalities such as diseased organs, cysts, tumors, etc. The volume of the data generated by these scanners is increasing the need for automatic image processing and recognition techniques. One such automatic technique is image segmentation, which includes the process of partitioning an image into multiple segments and locating objects of interest in the image as candidates for further evaluation or review. Assisted by advanced machine learning methods and deeper neural networks, image segmentation technology has made significant progress in recent years. But many challenges remain in the field due to practical constraints and complexities associated with the technology including domain mismatch, image quality variations, physiological differences across populations, etc.

SUMMARY

Described herein are neural network-based systems, methods and instrumentalities associated with image segmentation that may be implemented using one or more processors. An example system may comprise a first encoder neural network and a decoder neural network. The encoder network may be configured to receive a medical image comprising a visual representation of an anatomical structure and generate a representation (e.g., a latent representation) of the medical image, for example, through one or more down-sampling and/or convolution operations. The representation generated by the encoder network may indicate a plurality of features extracted from the medical image. The representation may be provided to the decoder network and the decoder network may generate a mask (e.g., a binary mask or a volumetric binary mask) for segmenting the anatomical structure from the medical image, for example, through one or more up-sampling and/or transposed convolution operations.

The decoder network may be pre-trained to learn a shape prior associated with the anatomical structure using training data representing a shape distribution of the anatomical structure. Once trained, the decoder network may be used to constrain an output of the first encoder network during training of the first encoder network. Such training of the first encoder network may be performed iteratively, e.g., in a cascading manner or using a recurrent neural network. During a present iteration of the training, the pre-trained decoder network may generate a segmentation mask associated with a training image based on a representation of the training image generated by the first encoder network in a preceding iteration of the training, and the first encoder network may predict an adjustment to the representation of the training image based on the segmentation mask generated by the decoder network and a ground truth associated with segmentation mask (e.g., based on a gradient descent of a loss function).

In examples, the decoder network may be co-trained with a second encoder network that is separate from the first encoder network. The co-training may comprise the second encoder network receiving a training image and generating an output to indicate a plurality of features of the training image, the decoding network predicting a segmentation mask associated with the training image based on the output of the second encoder network, and the second encoder network and the decoder network adjusting their respective parameters based on a loss function associated with the segmentation mask. In examples, the decoder network may be pre-trained without a corresponding encoder network and the pre-training comprises the decoder network receiving a latent representation of a training image as an input, the decoder network predicting a segmentation mask associated with the training image based on the latent representation, and the decoder network adjusting its parameters to minimize a loss between the predicted segmentation mask and a ground truth associated with the segmentation mask.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
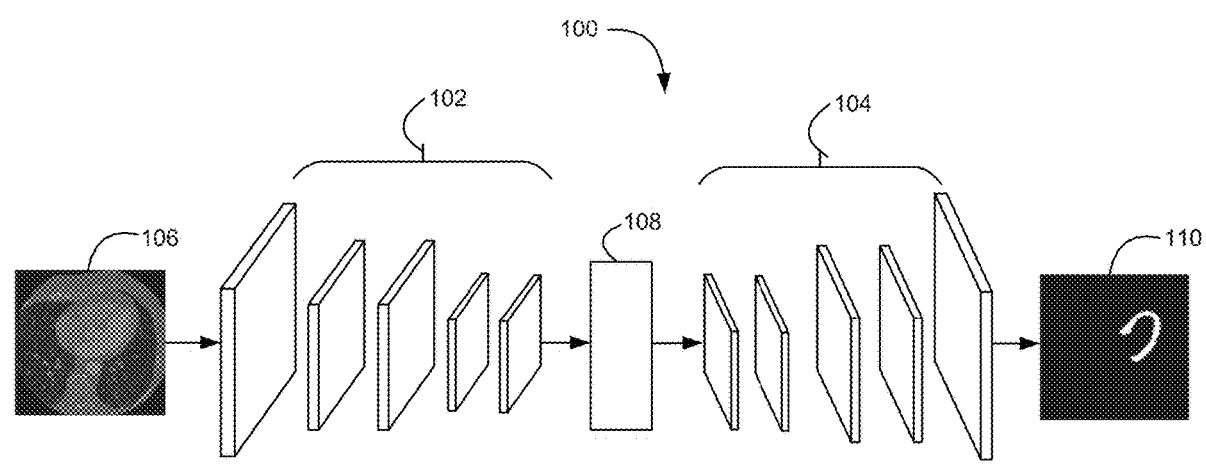
FIG. 1 is a simplified block diagram illustrating an example image segmentation system as described herein.

FIG. 1 is a block diagram illustrating an example neural network system 100 configured to perform image segmentation in accordance with one or more examples provided herein. The neural network system 100 may comprise an encoder network 102 and a decoder network 104. The encoder network 102 may be configured to receive an input image 106 such as a medical image (e.g., a CT or MRI scan) and produce a representation 108 (e.g., a low-resolution or low-dimension representation) of the input image that indicates one or more features of the input image. The encoder network 102 may comprise one or more neural networks such as one or more convolutional neural networks (CNNs) or fully convolutional neural networks (FCNs). Each of these neural networks may comprises a plurality of layers, and the encoder network 102 may be configured to produce the representation 108 by performing a series of down-sampling and/or convolution operations on the input image 106 through the layers of the neural networks. For example, as shown in FIG. 1, the encoder neural network 102 may comprise one or more convolutional layers, one or more pooling layers, and/or one or more fully connected layers.

Each of the convolutional layers may include a plurality of convolution kernels or filters configured to extract specific features from the input image 106. The convolution operation may be followed by batch normalization and/or non-linear activation, and the features extracted by the convolutional layers (e.g., in the form of one or more feature maps) may be down-sampled through the pooling layers and/or the fully connected layers (e.g., using a 2×2 window and a stride of 2) to reduce the redundancy and/or dimension of the features (e.g., by a factor of 2). The output of the encoder network 102 may include the representation 108, which may be in various forms depending on the specific task to be accomplished. For instance, the representation 108 may include a latent space variable Z (e.g., a vector) that represents a mapping between the input image 106 and a posterior distribution. In examples, the latent variable Z may be a fix-sized vector and each element of the vector may correspond to a respective probabilistic score for a category (e.g., for image classification), a respective set of coordinates of a bounding box (e.g., for object detection and localization), etc.

The decoder network 104 may be configured to receive the representation 108 produced by the encoder 102 and reconstruct (e.g., recover the details of) the input image 106 based on the representation 108. The decoder network 104 may generate a mask 110 (e.g., a pixel- or voxel-wise segmentation mask) for segmenting an object (e.g., a body part such as an organ) from the image 106. The decoder network 108 may comprise one or more neural networks such as one or more CNNs or FCNs each having a plurality of layers. Through these layers and a series of up-sampling and/or transpose convolution (e.g., deconvolution) operations, the decoder network 104 may interpret the representation 108 produced by the encoder network 102 and recover spatial details of the image, e.g., for pixel- or voxel-wise prediction. For instance, the decoder network 104 may comprise one or more un-pooling layers and one or more convolutional layers. Using the un-pooling layers, the decoder network 104 may up-sample the representation 108 produced by the encoder network 102, e.g., based on pooled indices stored by the encoder. The up-sampled representation may then be processed through the convolutional layers (e.g., using 3×3 transposed convolutional kernels with a stride of 2) to produce a plurality of dense feature maps (e.g., up-scaled by a factor of 2) before batch normalization is applied to each feature map to obtain a high dimensional representation of the input image 106. The output of the decoder network 104 may include the segmentation mask 110 for delineating one or more regions (e.g., one or more organs, background, etc.) of the image 106. In examples, such a segmentation mask may correspond to a multi-class, pixel/voxel-wise probabilistic maps in which pixels or voxels belonging to each of the multiple classes are assigned a high probability value indicating the classification of the pixels/voxels. In cases of two-dimensional (2D) images, the output of the decoder network 104 may indicate boundary points of the delineated regions while in cases of three-dimensional (3D) images, the output of the decoder network 104 may indicate 3D mesh surfaces associated with the delineated regions.

The neural network system 100 (e.g., the encoder network 102 and/or the decoder network 104) may be implemented using one or more processors, one or more storage devices, and/or other suitable accessory devices such as display devices, communication devices, input/output devices, etc. The storage devices may be configured to store instructions that, when executed by the one or more processors, cause the one or more processors to execute the functions described herein. The one or more processors may include a central processing unit (CPU), a graphics processing unit (GPU), a microcontroller, a reduced instruction set computer (RISC) processor, an application specific integrated circuit (ASIC), an application-specific instruction-set processor (ASIP), a physics processing unit (PPU), a digital signal processor (DSP), a field programmable gate array (FPGA), or a combination thereof. The one or more storage devices may include volatile or non-volatile memory such as semiconductor memory (e.g., electrically programmable read-only memory (EPROM), electrically erasable programmable read-only memory (EEPROM), etc.), flash memory, a mass storage device (e.g., a magnetic disk such as an internal hard disk, a removable disk, a magneto-optical disk, a CD-ROM or DVD-ROM disk, etc.).

In addition, it should be noted that although the examples are described herein with reference to various types of neural networks, various types of layers, and/or various tasks being performed by certain types of neural networks or layers, the references are made merely for illustration purposes and not meant to limit the scope of the disclosure. For example, in certain implementations, the encoder network 102 and/or the decoder network 104 may not include a fully connected layer and may still be able to perform the functions described herein. Further, even though the neural network system 100 is shown and described as having an encoder-decoder structure, the implementation of the neural network system 100 is not limited to one specific structure. For example, the neural network system 100 may be implemented using an autoencoder structure, a variational autoencoder structure, and/or other types of structures suitable for the functionality described herein. When a variational autoencoder is used, the representation (e.g., latent variable z) may be regularized using a prior normal distribution.

The encoder network 102 and/or the decoder network 104 may be trained to learn and use a shape prior during image segmentation to prevent or reduce problems associated with over-segmentation (e.g., segmentation leakage) and/or under-segmentation (e.g., due to domain miss-matching or lack of training data), and to improve the success rate of the segmentation operation. When referred to herein, a shape prior may include knowledge about the shapes of objects to be segmented from an image. These objects may include anatomical structures of a human body (e.g., such as organs) and/or abnormalities in the human body (e.g., such as cysts, tumors, polyps, etc.) while the shapes may include partial and complete shapes. Once learned, the shape prior may be used to constraint the output of the encoder network 102 and/or the decoder network 104, for example, during both training and actual operation of the neural network system 100.

In examples, the decoder network 104 may be trained before the encoder network 102 to learn the shape prior and the pre-trained decoder network 104 may then be used to train (e.g., optimize the parameters of) the encoder neural network 102. The training of the decoder network 104 may be conducted with or without a corresponding encoder network, as illustrated by FIG. 2A and FIG. 2B.

Figure 2:
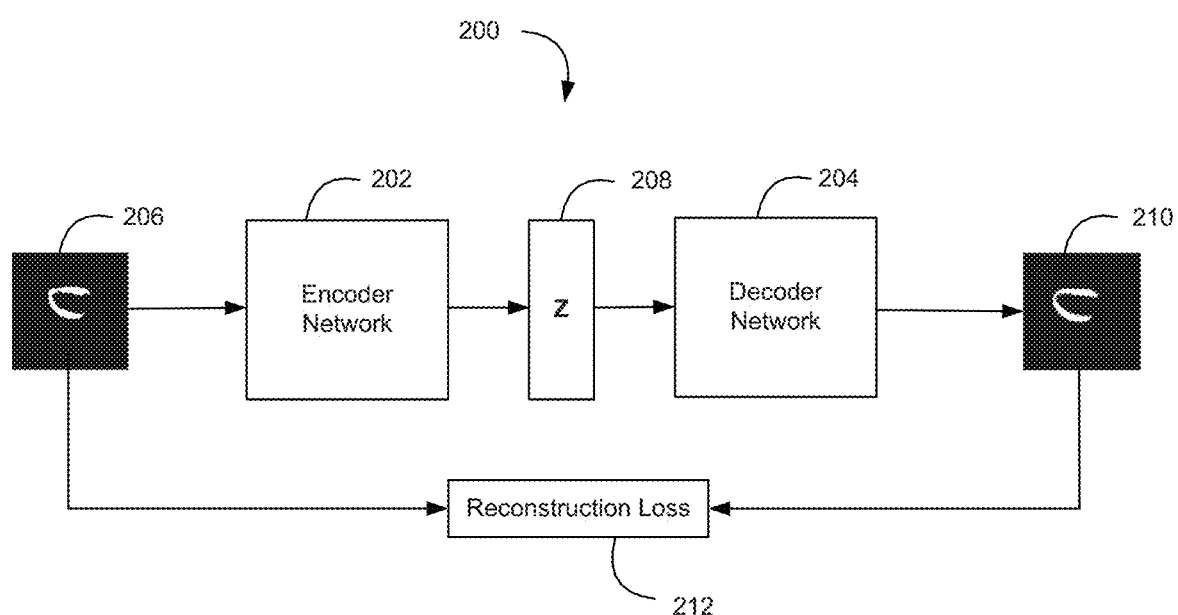
FIG. 2 is a simplified block diagram illustrating the training of an example decoder network with a corresponding encoder network.

FIG. 2 is a simplified block diagram illustrating an example process 200 for training a decoder network 204 (e.g., the decoder network 104) with a corresponding encoder network 202. The encoder network 202 may be an encoder network configured for purposes of training the decoder network 204 and as such may be a separate network from the encoder network 102 shown in FIG. 1. The encoder network 202 and the decoder network 204 may respectively comprise one or more CNNs or FCNs each having a plurality of layers (e.g., similar to the encoder network 102 and the decoder network 104, respectively). The plurality of layers of the encoder network 202 and the decoder network 204 may be assigned respective initial operating parameters (e.g., filtering weights) that may be, for example, sampled from one or more probability distributions or based on parameter values of another network with a similar architecture.

The training process 200 may be conducted using a training dataset comprising sample segmentation masks associated with a target anatomical structure (e.g., a human organ). The sample segmentation masks in the training dataset) may represent a shape distribution of the target anatomical structure (e.g., the sample segmentation masks may be associated with different shape variations of the target anatomical structure in the general population) and as such the decoder network 204 may learn the shape prior of the target structure by processing the sample segmentation masks. For example, the training dataset may comprise annotated segmentation masks associated with different shape variations of the target anatomical structure. During the training, the encoder network 202 may receive an input mask 206 from the training dataset. The encoder network 202 may process the input mask 206 through a series of down-sampling and/or convolution operations (e.g., via the plurality of layers of the encoder network) to extract features from the input mask 206 and generate a representation 208 (e.g., a latent variable Z) indicating the extracted features of the input mask. The representation 208 may be provided to the decoder network 204, which in response may reconstruct a segmentation mask 210 based on the representation 208. The reconstruction may be performed through the layers of the decoder network 204 and a series of up-sampling and transposed convolution (e.g., deconvolution) operations, e.g., similar to those described in association with the decoder network 104.

The reconstructed segmentation mask 210 may be compared to the annotated input mask 206 (e.g., as a ground truth) to determine a reconstruction loss 212. The reconstruction loss 212 may be calculated based on various mathematical formulas including, for example, mean squared error (MSE), L1/L2 norm, etc. In response to determining the reconstruction loss 212, the encoder network 202 and the decoder network 204 may adjust their respective operating parameters (e.g., weights), for example, based on a gradient descent associated with the reconstruction loss to reduce the reconstruction loss 212. The adjustment of the parameters may be performed, for example, by backpropagating the reconstruction error through the encoder and decoder networks. The training process 200 may then repeat until one or more training termination criteria are satisfied (e.g., after completing a pre-determined number of training iterations, after the reconstruction loss falls below a predetermined threshold, etc.).

Figure 3:
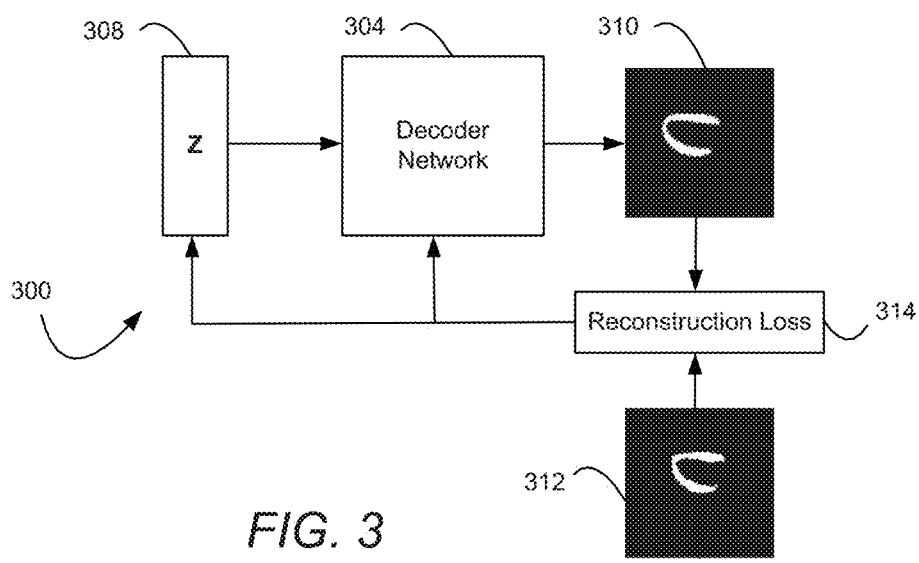
FIG. 3 is a simplified block diagram illustrating the training of an example decoder network without a corresponding encoder network.

FIG. 3 is a simplified block diagram illustrating an example process 300 for training a decoder network 304 (e.g., the decoder network 104) without a corresponding encoder network. The training process 300 may be conducted using a representation (e.g., a latent variable Z) 308 associated with a human anatomical structure (e.g., a human organ). The representation 308 may be initialized, for example, randomly from a normal distribution with a standard deviation. During the training, the decoder network 304 may receive the representation 308 and process the representation through a series of up-sampling and/or deconvolution operations (e.g., via the plurality of layers of the decoder network) to predict a segmentation mask 310 for the concerned anatomical structure based on the representation 308. The decoder network 304 may compare the predicted segmentation mask 310 to an expected segmentation mask 312 (e.g., a ground truth) for the anatomical structure to determine a reconstruction loss 314. The reconstruction loss 314 may be determined, for example, in accordance with a loss or objective function (e.g., MSE, L1/L2 norm, etc.) associated with the decoder network 304. In response to determining the reconstruction loss 314, the decoder network 304 may adjust its operating parameters (e.g., weights), for example, based on a gradient descent associated with the loss function to reduce the reconstruction loss 314. The representation 308 may also be adjusted (e.g., optimized) based on the reconstruction loss 314, for example, using a suitable gradient descent optimization method. The training process 300 may then repeat until one or more training termination criteria are satisfied (e.g., after completing a pre-determined number of training iterations, after the reconstruction loss falls below a predetermined threshold, etc.).

A pre-trained decoder network (e.g., the decoder network 104 of FIG. 1. or the decoder network 204 of FIG. 2) may be used in a segmentation system (e.g., the neural network system 100 of FIG. 1) to segment an anatomical structure from an input image. The pre-trained decoder network may also be used to train an encoder network (e.g., the encoder network 102) of the segmentation system. For example, the pre-trained decoder network may be used to constrain the output of such an encoder network during training of the encoder network and the constraint imposed by the decoder network may cause the encoder network to learn its parameters in accordance with the shape prior acquired by the decoder network. In examples, the encoder network may be trained to directly predict a latent representation (e.g., a latent variable Z) based on the shape prior acquired by the pre-trained decoder network (e.g., using one or more suitable regression techniques). In examples, the encoder network may be trained to iteratively predict the latent variable Z (e.g., using one or more suitable optimization techniques).

Figure 4:
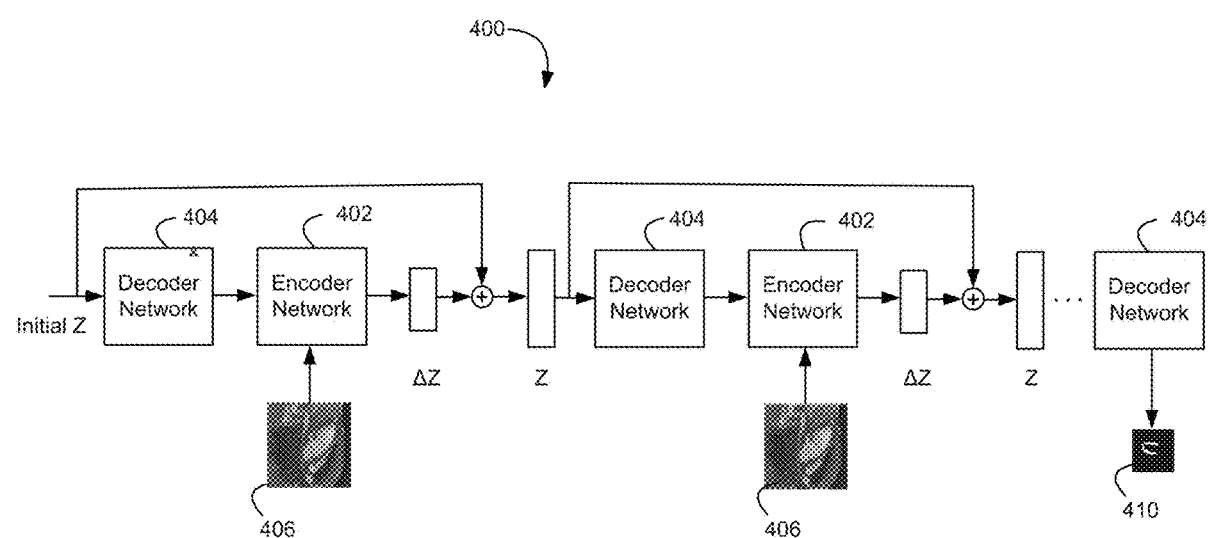
FIG. 4 is a simplified block diagram illustrating an example segmentation system comprising a cascading neural network.

FIG. 4 is a simplified block diagram illustrating an example segmentation system 400 comprising an encoder network 402 (e.g., the encoder network 102 of FIG. 1) and a pre-trained decoder 404 (e.g., the decoder network 104 of FIG. 1, the decoder network 204 of FIG. 2 or the decoder network 304 of FIG. 3) that has learned a shape prior. The segmentation system 400 may be trained with an objective of enabling the encoder network 402 to optimize the following equation through an iterative process (e.g., a meta-learning process):

$$Z_n = Z_{n-1} + \Delta Z \qquad 1)$$

where Z in the equation may denote a representation (e.g., a latent space representation) of the features of a training image and $\Delta Z$ may denote the gradient output of a function G.

As shown in FIG. 4, the segmentation system 400 may comprise a cascade neural network comprising one or more instances of the encoder network 402 and the decoder network 404, and the training of the system may be performed through one or more iterations. In a first iteration, a latent variable Z associated with a training image 406 may be initialized, e.g., based on a normal distribution with a standard deviation. The latent variable Z may be provided to the pre-trained decoder network 404 that has acquired its parameters in accordance with a shape prior associated with a target object of the training image 406, as described herein.

Using the pre-acquired parameters (which may be fixed during the training of the encoder 402), the decoder network 404 may reconstruct image data and/or a segmentation mask corresponding to the training image 406 based on the initial latent variable Z. The output of the decoder network 404 may feed into the encoder network 402. In examples, both the reconstructed image data and segmentation mask may be provided to the encoder network 402 (e.g., via respective first and second input channels). In examples, the reconstructed image data may be provided to the encoder network 402 without the segmentation mask. Based on reconstructed image input and/or segmentation mask and the training image 406, the encoder network may predict a $\Delta Z$, for example, as the gradient output of a loss function G (e.g., based on MSE or L1/L2 norm). Once $\Delta Z$ is predicted, the initial latent variable Z may be updated in accordance with equation 1), and the updated latent variable Z may be provided as an input to a second iteration of the training. The operations described above may then be repeated and the encoder network 402 may adjust its parameters (e.g., weights) during the iterative process with an objective of minimizing the difference between $Z_n$ and $Z_{n-1}$ so that the decoder network 404 may generate a segmentation mask 410 that conform to the shape prior of the target object. The operations illustrated in FIG. 4 may be performed iteratively until one or more termination criteria are satisfied. For example, the operations may be terminated after a predetermined number of iterations have been completed or until $\Delta Z$ falls below a threshold (e.g., a predetermined threshold).

Figure 5:
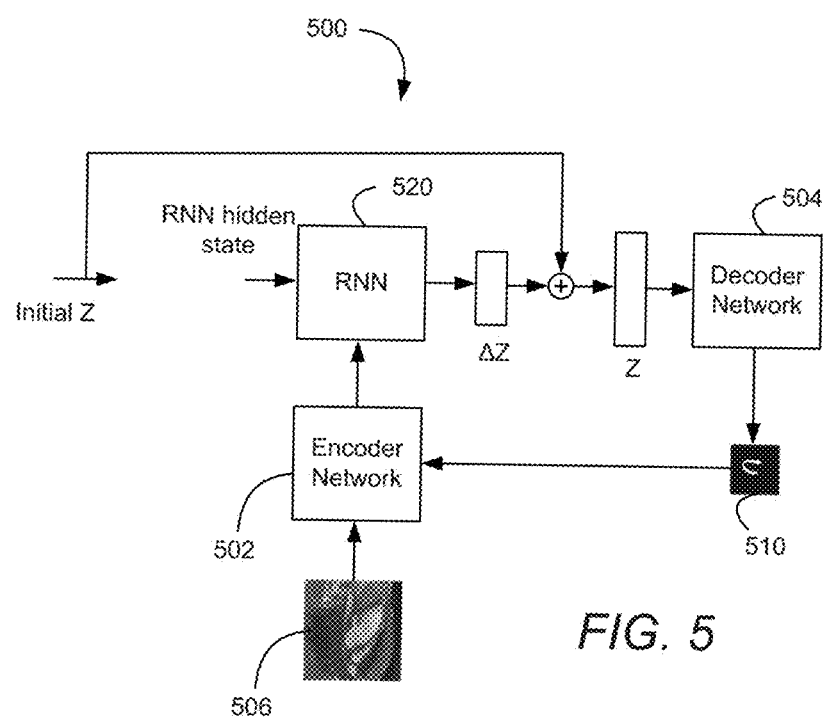
FIG. 5 is a simplified block diagram illustrating an example segmentation system comprising a recurrent neural network.

The segmentation system described herein may also be implemented using a recurrent neural network (RNN). FIG. 5 is a simplified block diagram illustrating an example segmentation system 500 comprising an RNN. Similar to the segmentation system 400, the segmentation system 500 may comprise a pre-trained decoder 504 (e.g., the decoder network 104 of FIG. 1, the decoder network 204 of FIG. 2 or the decoder network 304 of FIG. 3) that has learned a shape prior, and an encoder network 502 that may be trained to optimize the equation 1) described above.

During training of the segmentation system 500, a latent variable Z associated with a training image 506 may be initialized, e.g., based on a normal distribution with a standard deviation. The latent variable Z may be provided to the pre-trained decoder network 504 that has acquired its operating parameters (e.g., weights) through pre-training to learn a shape prior associated with a target object of the training image 506, as described herein. Using these parameters (which may be fixed during the training of the encoder network 502), the decoder network 504 may reconstruct image data and/or a segmentation mask based on the latent variable Z. The encoder network 502 may receive the image data reconstructed by the decoder network 404 (e.g., with or without the segmentation mask predicted by the decoder network), along with the training image 506. Based on the reconstructed image data and the original image, the encoder network 502 may make a prediction for the encoded features and provide the prediction to the RNN 520.

The RNN 520 may treat the output of the encoder network 502 as a current RNN state and generate a $\Delta Z$ that may be used to compute an updated version of Z based on equation 1) described above. The operations described above may then be repeated, where each iteration of the training is realized by a respective unrolling of the RNN 520. During this iterative process, the encoder network 502 may adjust its parameters (e.g., weights) with an objective of minimizing the difference between $Z_n$ and $Z_{n-1}$ so that the decoder network 504 may generate a segmentation mask 510 that conforms to the learned shape prior of the target object. The operations illustrated in FIG. 5 may be performed iteratively until one or more termination criteria are satisfied. For example, the operations may be terminated after a predetermined number of iterations have been completed or until $\Delta Z$ falls below a threshold (e.g., a predetermined threshold).

Each of the neural networks described herein may comprise multiple layers including an input layer, one or more convolutional layers, one or more non-linear activation layers, one or more pooling layers, one or more fully connected layers, and/or an output layer. Each of the layers may correspond to a plurality of filters (e.g., kernels) and each filter may be designed to detect (e.g., learn) a set of keypoints that collectively represent a respective feature or pattern. The filters may be associated with respective weights that, when applied to an input, produce an output indicating whether certain visual features or patterns have been detected. The weights associated with the filters may be learned by the neural networks through a training process that comprises inputting a large number of images from one or more training datasets to the neural networks, calculating differences or losses resulting from the weights currently assigned to the filters (e.g., based on an objective function such as mean squared error or L1 norm, a margin based loss function, etc.), and updating the weights assigned to the filters so as to minimize the differences or losses (e.g., based on stochastic gradient descent).

Figure 6:
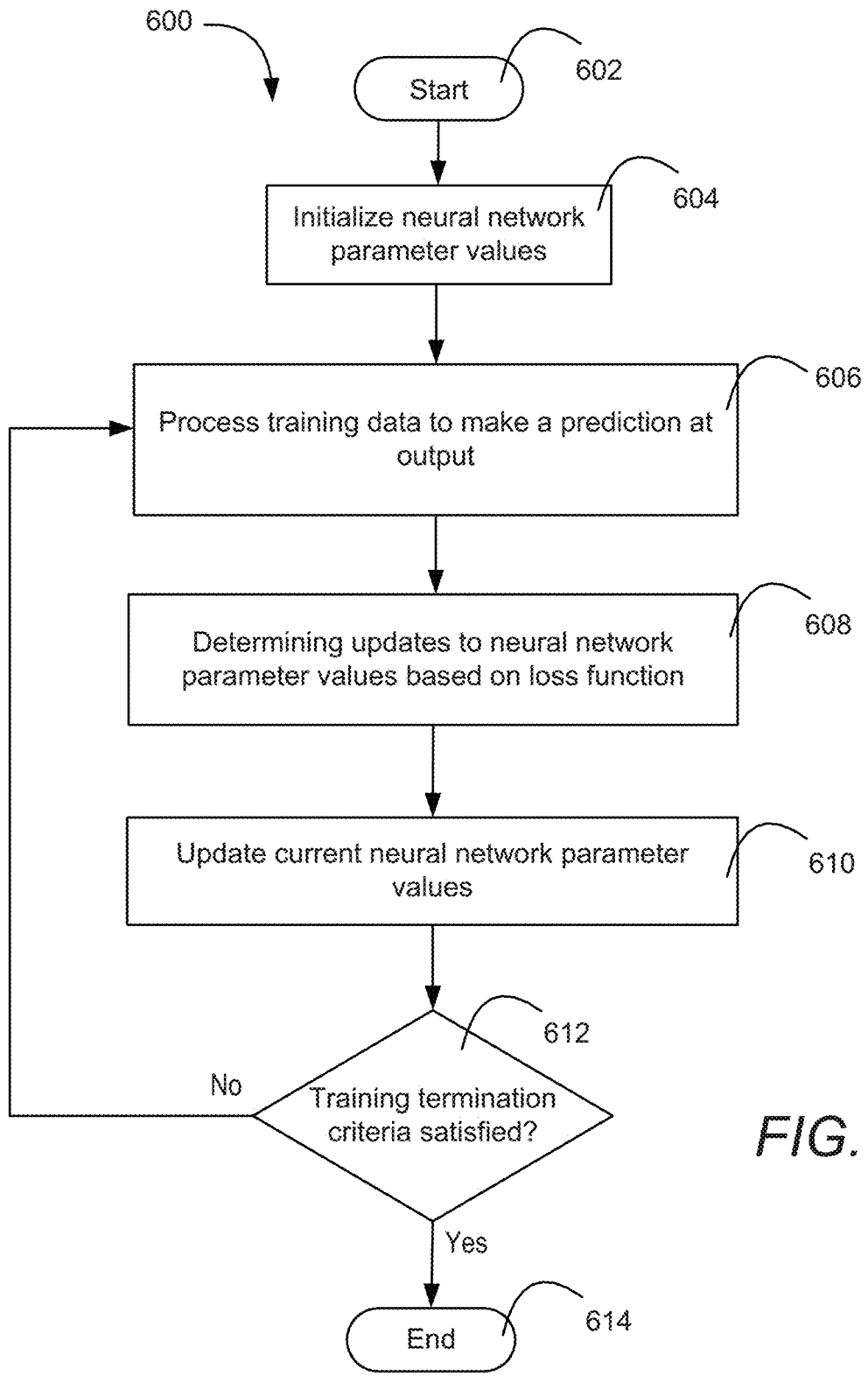
FIG. 6 is a flow diagram illustrating an example neural network training process.

FIG. 6 is a flow diagram of an example process 600 that may be implemented and executed during training of one or more of the neural networks described herein. The process 600 may be performed by a system of one or more computers (e.g., one or more processors) located in one or more locations. The process may start at 602 and, at 604, the system may initialize the operating parameters of the neural network (e.g., weights associated with one or more layers of the neural network). For example, the system may initialize the parameters based on samples from one or more probability distributions or parameter values of another neural network with a similar architecture. At 606, the system may process a training image and/or other training data such as a latent variable described herein using the current parameter values assigned to the layers. A prediction may be made as a result of the processing and at 608, the system may determine updates to the current parameter values, e.g., based on an objective or loss function and a gradient descent of the function. As described herein, the objective function may be designed to minimize the difference between the prediction and a ground truth. The objective function may be implemented using, for example, mean squared error, L1 norm, etc. At 610, the system may update the current values of the neural network parameters, for example, through a backpropagation process. At 612, the system may determine whether one or more training termination criteria are satisfied. For example, the system may determine that the training termination criteria are satisfied if the system has completed a pre-determined number of training iterations, or if the change in the value of the loss function between two training iterations falls below a predetermined threshold. If the determination at 612 is that the training termination criteria are not satisfied, the system may return to 606. If the determination at 612 is that the training termination criteria are satisfied, the system may end the training process 600 at 614.

For simplicity of explanation, the operation of the example system is depicted and described herein with a specific order. It should be appreciated, however, that these operations may occur in various orders, concurrently, and/or with other operations not presented or described herein. Furthermore, it should be noted that not all operations that the system is capable of performing are depicted and described herein, and not all illustrated operations are required to be performed by the system.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A neural network system implemented using one or more processors, the neural network system comprising:
   a first encoder neural network configured to:
      receive a medical image comprising a visual representation of an anatomical structure; and
      generate a representation of the medical image, the representation indicating a plurality of features extracted from the medical image; and
   a decoder neural network configured to:
      receive the representation of the medical image from the first encoder neural network; and
      generate a mask for segmenting the anatomical structure from the medical image based on the representation of the medical image;
   wherein the decoder neural network is trained before the first encoder neural network to learn a shape prior associated with the anatomical structure using a training dataset that represents a shape distribution of the anatomical structure, and wherein, during training of the first encoder neural network, parameters of the decoder neural network are fixed and the decoder neural network is used to constrain an output of the first encoder neural network.

2. The neural network system of claim 1, wherein the first encoder neural network is trained iteratively and, during a present training iteration of the first encoder neural network:
   the decoder neural network is used to generate a segmentation mask associated with a training image based on a representation of the training image generated by the first encoder neural network in a preceding training iteration of the first encoder neural network; and
   the first encoder neural network predicts an adjustment to the representation of the training image based on the segmentation mask generated by the decoder neural network and a ground truth associated with the segmentation mask.

3. The neural network system of claim 2, wherein the representation of the training image comprises a latent space representation of the training image.

4. The neural network system of claim 2, wherein the training of the first encoder neural network comprises deriving an initial representation of the training image and providing the initial representation of the training image to the decoder neural network so as to obtain an initial prediction of the segmentation mask.

5. The neural network system of claim 2, wherein multiple instances of the first encoder neural network and the decoder neural network are arranged in a cascading manner in the neural network system.

6. The neural network system of claim 2, wherein the first encoder neural network comprises a recurrent neural network (RNN).

7. The neural network system of claim 1, wherein the decoder neural network is co-trained with a second encoder neural network and the co-training comprises:
   the second encoder neural network receiving a training image and generating an output to indicate a plurality of features of the training image;
   the decoder neural network predicting a segmentation mask associated with the training image based on the output of the second encoder neural network; and
   the second encoder neural network and the decoder neural network adjusting their respective parameters based on a loss function associated with the segmentation mask.

8. The neural network system of claim 1, wherein the decoder neural network is trained without a corresponding encoder neural network and the training of the decoder neural network comprises:
   the decoder neural network receiving a latent representation of a training image as an input;
   the decoder neural network predicting a segmentation mask associated with the training image based on the latent representation; and
   the decoder neural network adjusting its parameters to minimize a loss between the predicted segmentation mask and a ground truth associated with the segmentation mask.

9. The neural network system of claim 1, wherein the representation of the medical image generated by the first encoder neural network comprises a latent variable.

10. The neural network system of claim 1, wherein, during the training of the first encoder neural network, the decoder neural network is used to constrain the output of the first encoder neural network based on the shape prior of the anatomical structure learned by the decoder neural network.

11. A method for segmenting a medical image comprising a visual representation of an anatomical structure, the method comprising:
   receiving, via a first encoder neural network, the medical image;
   generating, via the first encoder neural network, a representation of the medical image, the representation indicating a plurality of features extracted from the medical image;
   receiving, at a decoder neural network, the representation of the medical image; and
   generating, via the decoder neural network, a mask for segmenting the anatomical structure from the medical image based on the representation of the medical image;

wherein the decoder neural network is trained before the first encoder neural network to learn a shape prior associated with the anatomical structure using training data representing a shape distribution of the anatomical structure, and wherein, during training of the first encoder neural network, parameters of the decoder neural network are fixed and the decoder neural network is used to constrain an output of the first encoder neural network.

12. The method of claim 11, wherein the first encoder neural network is trained iteratively and, during a present training iteration of the first encoder neural network, the decoder neural network generates a segmentation mask associated with a training image based on a representation of the training image generated by the first encoder neural network in a preceding training iteration of the first encoder neural network and the first encoder neural network predicts an adjustment to the representation of the training image based on the segmentation mask generated by the decoder neural network and a ground truth associated with the segmentation mask.

13. The method of claim 12, wherein the representation of the training image comprises a latent space representation of the training image.

14. The method of claim 12, wherein the training of the first encoder neural network comprises deriving an initial representation of the training image and providing the initial representation of the training image to the decoder neural network so as to obtain an initial prediction of the segmentation mask.

15. The method of claim 12, wherein the mask for segmenting the anatomical structure is generated using multiple instances of the first encoder neural network and the decoder neural network arranged in a cascading manner.

16. The method of claim 12, wherein the first encoder neural network comprises a recurrent neural network (RNN).

17. The method of claim 11, wherein the decoder neural network is co-trained with a second encoder neural network and the co-training comprises:
the second encoder neural network receiving a training image and generating an output to indicate a plurality of features of the training image;
the decoder neural network predicting a segmentation mask associated with the training image based on the output of the second encoder neural network; and
the second encoder neural network and the decoder neural network adjusting their respective parameters based on a loss function associated with the segmentation mask.

18. The method of claim 11, wherein the decoder neural network is trained without a corresponding encoder neural network and the training of the decoder neural network comprises:
the decoder neural network receiving a latent representation of a training image as an input;
the decoder neural network predicting a segmentation mask associated with the training image based on the latent representation; and
the decoder neural network adjusting its parameters to minimize a loss between the predicted segmentation mask and a ground truth associated with the segmentation mask.

19. The method of claim 11, wherein the representation of the medical image generated by the first encoder neural network comprises a latent variable.

20. A method of training a neural network system for image segmentation, the neural network system comprising a decoder neural network and an encoder neural network, the method comprising:
training the decoder neural network before the encoder neural network to learn a shape prior associated with an anatomical structure, wherein the training of the decoder neural network is performed using a training dataset that represents a shape distribution of the anatomical structure, and wherein the training of the decoder neural network comprises:
providing the decoder neural network with a representation of a medical image comprising a visual representation of the anatomical structure, the representation indicating a plurality of features of the medical image;
causing the decoder neural network to predict a first segmentation mask based on the provided representation; and
causing the decoder neural network to adjust its parameters to minimize a first loss between the first segmentation mask and a ground truth associated with the first segmentation mask; and
training the encoder neural network utilizing the decoder neural network, wherein the encoder neural network is trained iteratively, wherein the parameters of the decoder neural network are fixed during the training of the encoder neural network, and wherein a present training iteration of the encoder neural network comprises:
causing the decoder neural network to predict a second segmentation mask associated with a training image based on a representation of the training image obtained during a preceding training iteration of the encoder neural network;
causing the encoder neural network to update its parameters and predict an adjustment to the representation of the training image based on a difference between the second segmentation mask predicted by the decoder neural network and a ground truth associated with the second segmentation mask; and
obtaining an adjusted representation of the training image based on the adjustment predicted by the encoder neural network and the representation of the training image obtained during the preceding training iteration of the encoder neural network.

* * * * *